United States Patent [19]
Takahashi et al.

[11] Patent Number: 6,054,578
[45] Date of Patent: Apr. 25, 2000

[54] METHOD FOR ADSORBING CHOLESTEROL OXIDE, AND PROCESS FOR PRODUCING FOODS CONTAINING CHOLESTEROL OR CHOLESTEROL OXIDE

[75] Inventors: Taro Takahashi; Hirokazu Maeda, both of Tsukuba-gun; Toshiaki Aoyama, Izumisano; Kyouichi Osada; Shingo Nakamura, both of Hirosaki, all of Japan

[73] Assignee: Fuji Oil Co., Ltd., Japan

[21] Appl. No.: 09/121,785

[22] Filed: Jul. 23, 1998

[30] Foreign Application Priority Data

Aug. 5, 1997 [JP] Japan .................. 9-210449

[51] Int. Cl.$^7$ ............... C07H 1/00; A23C 9/14
[52] U.S. Cl. ............ 536/123.1; 536/124; 536/128; 514/54; 424/195.1; 426/271; 426/658
[58] Field of Search ................. 536/123.1, 124, 536/128; 514/54; 426/271, 658; 424/195.1

[56] References Cited

U.S. PATENT DOCUMENTS 5,039,541 8/1991 Keen ........................ 426/417
5,262,167 11/1993 Vegesna et al. ............ 424/439

FOREIGN PATENT DOCUMENTS 59-210850 11/1984 Japan .
6-256402 9/1994 Japan .

OTHER PUBLICATIONS

HCAPLUS abstract AN 1995:308746 of JP 06256402, Sep. 13, 1994.

*Primary Examiner*—Kathleen K. Fonda
*Attorney, Agent, or Firm*—Wallenstein & Wagner, Ltd.

[57] ABSTRACT

A cholesterol oxide adsorbing agent whose effective component is a plant-derived water-soluble polysaccharide, a process for producing the cholesterol oxide adsorbing agent characterized by extraction of the polysaccharide from the plant at from 80° C. to 130° C., a method of adsorbing cholesterol oxide using the plant-derived water-soluble polysaccharide, and a process for producing foods characterized by adding the plant-derived water-soluble polysaccharide to foods containing cholesterol or cholesterol oxide.

3 Claims, 3 Drawing Sheets

METHOD FOR ADSORBING CHOLESTEROL OXIDE, AND PROCESS FOR PRODUCING FOODS CONTAINING CHOLESTEROL OR CHOLESTEROL OXIDE

BACKGROUND OF THE INVENTION

1. Field of the Invention

The present invention relates to a cholesterol oxide adsorbing agent, a process for its production, a method for adsorbing cholesterol oxide and a process for producing foods containing cholesterol or cholesterol oxide.

2. Description of the Related Art

Cholesterol oxide has an effect on body functions similar to fatty acid peroxides and has been implicated as a trigger causing various diseases, as well as aging. Cholesterol oxide, which has such a harmful effect on the body, is produced in significant amounts during processing of animal product foods, and it has been reported that about 30% is absorbed in the small intestine, resulting in disturbance to the cholesterol and fatty acid metabolism.

In the light of this background, and with the increasing ingestion of processed animal product foods, research has continued in the hope of achieving a rapid understanding of the mechanism involved, in order to establish a means for reducing absorption of cholesterol oxide into the body and suppressing its physiological effects; it is highly important for public health to elucidate the presence of a food component with such a physiological function.

Up to the present time there have been reported cholesterol oxide adsorbing agents composed mainly of acidic polysaccharides as described in Japanese Unexamined Patent Publication No. 3-30667 and No.8-253502, as food components which inhibit absorption of cholesterol oxide in foods or control its physiological action.

However, the process described in Japanese Unexamined Patent Publication No. 3-30667 uses polysaccharides produced only from special yeast mutants, and is therefore associated with problems of dubious safety and poor yield. In addition, the process described in Japanese Unexamined Patent Publication No. 8-253502 involves synthesis of sulfated polysaccharides by a chemical method, and is therefore associated with problems of safety including the presence of residual unreacted components.

Thus, no fully satisfactory solution has yet been found for food materials which are safe and economical to use as adsorbing agents for cholesterol oxide which so adversely affects the body, or for a process for their production.

SUMMARY OF THE INVENTION

As a result of diligent research in light of these circumstances, the present inventors have found that a water-soluble polysaccharide extracted from soybean has a very strong adsorbent property for cholesterol oxide, and that this polysaccharide can be easily extracted from soybean with hot water at 130° C. or below. The present invention has been completed on the basis of this finding.

In other words, the present invention relates to a cholesterol oxide adsorbing agent whose effective component is a plant-derived water-soluble polysaccharide, to a process for producing the cholesterol oxide adsorbing agent characterized by extraction of the polysaccharide from the plant at from 80° C. to 130° C., to a method of adsorbing cholesterol oxide using the plant-derived water-soluble polysaccharide, and to a process for producing foods characterized by adding the plant-derived water-soluble polysaccharide to foods containing cholesterol or cholesterol oxide.

DESCRIPTION OF THE PREFERRED EMBODIMENTS

Figure 1:
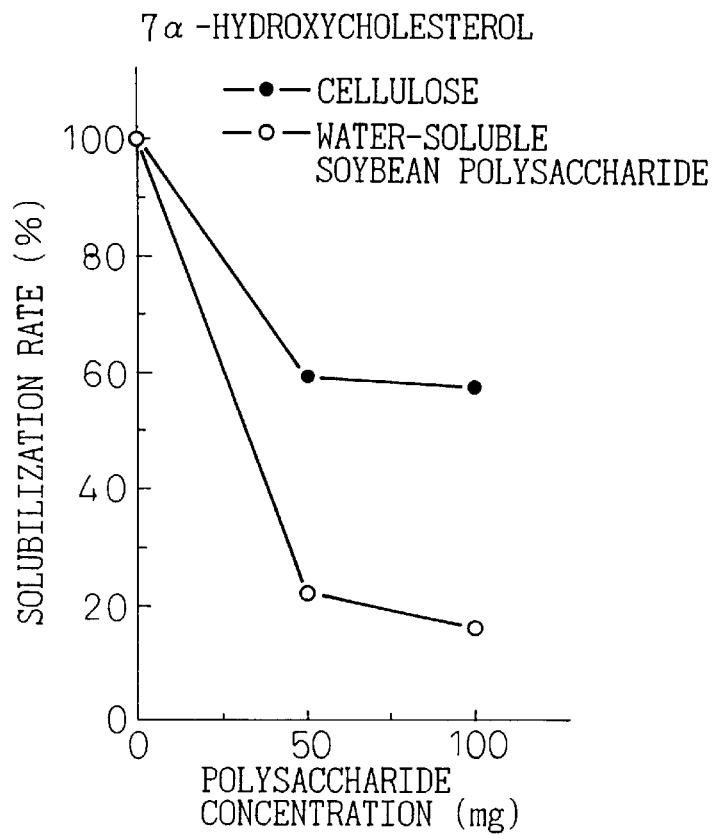
FIG. 1 is a graph showing the micelle solubilization rate for 7α-hydroxycholesterol

The water-soluble polysaccharide of the invention is derived from beans, and preferably from soybean, especially the cotyledon thereof.

The water-soluble polysaccharide used may have a molecular weight of any value, but preferably it has an average molecular weight of a few tens of thousand to a few million, and specifically from 50,000 to 1,000,000. Here, the average molecular weight of the water-soluble polysaccharide is the value determined by the limiting viscosity method whereby the viscosity is measured in a 0.1 molar $NaNO_3$ solution using standard pullulan (Showa Denko, KK.) as the standard substance. The measurement of uronic acid was made by the Blumenkrantz method, and measurement of the neutral saccharides was made by the GLC method after alditol acetate conversion.

The water-soluble polysaccharide may be obtained by water extraction from the polysaccharide-containing raw material, or in some cases by heating and elution under acid or alkali conditions or decomposition and elution with an enzyme. The following is an example of a process for producing a water-soluble polysaccharide.

The raw material may be from a plant, for example, the shell of an oily seed such as soybean, palm, coconut, corn, cottonseed, rapeseed, safflower, etc., usually with the oil and protein removed, or the lees from a grain such as rice or wheat, usually with the starch, etc. removed, or the pressed lees of sugar cane, beet, etc. If the raw material is soybean, it may be obtained as the bean-curd lees produced during manufacture of tofu, soybean milk or separated soy protein.

The raw material is thermally decomposed under acidic or alkali conditions, preferably at a pH near the isoelectric point of the protein, preferably at a temperature from 80° C. to 130° C. and more preferably from 100° C. to 130° C. and, after separating out the water-soluble fraction, it is either dried immediately, or dried after being subjected to, for example, active carbon treatment, resin adsorption treatment or ethanol precipitation treatment to remove the hydrophobic substances or low molecular substances, to obtain the water-soluble polysaccharide.

According to the invention, the water-soluble polysaccharide may be used alone as a cholesterol oxide adsorbing agent, but it may also be used in combination with known cholesterol and cholesterol oxide absorption inhibitors and adsorbing agents to compensante for their deficiencies.

As known cholesterol and cholesterol oxide absorption inhibitors and adsorbing agents there may be mentioned, in addition to the acidic polysaccharide described in Japanese Unexamined Patent Publication No. 3-30667, aminopolysaccharides such as chitin and chitosan, and ion exchange resins such as cholestymin and cholestipol.

According to the invention, the plant-derived water-soluble polysaccharide is added to the food containing the cholesterol or cholesterol oxide, so that the cholesterol oxide produced when the food is cooked by boiling, baking, steaming, frying or deep-frying, is adsorbed by the water-soluble polysaccharide and excreted out of the body. As a result, by preadding the plant-derived water-soluble polysaccharide to the food containing the cholesterol or cholesterol oxide, it is possible to produce foods with low contents cholesterol to be absorbed. Examples of such foods containing cholesterol or cholesterol oxide include animal oils such as lard used for frying or deep frying of french fries and the like, as well as various livestock and marine products such as beef, pork, chicken, fish and shellfish, food products utilizing these foods, and butter, margarine, shortening, cream, mayonnaise, curry sauce, etc.

The amount of the plant-derived water-soluble polysaccharide to be added to these foods cannot be generally specified as it will differ depending on the type of food, i.e. the cholesterol content of the food, and the differences in changes which occur with heating, but the water-soluble polysaccharide is preferably added at about a 5-fold volume to a 50-fold volume of the estimated cholesterol content for most foods.

Embodiments of the present invention will now be explained by way of examples which, however, are only exemplary and are not intended to limit the spirit of the invention. In these examples, the references to "parts" and "%" are based on a weight standard.

Examples 1–3
Preparation of water-soluble soybean polysaccharide (A)

(Example 1)

A two-fold amount of water was added to raw bean-curd lees obtained during the production of separated soybean protein, the pH was adjusted to 4.5 with hydrochloric acid, and heat extraction was performed at 120° C. for 1.5 hours. After cooling, the supernatant and precipitate were separated by centrifugation (10,000 G×30 min). An equivalent weight of water was added to the separated precipitate portion, and after a second centrifugation, the supernatant was combined with the previous supernatant, passed through an active carbon column, and subjected to purification treatment and then drying to obtain a water-soluble soybean polysaccharide (A).

Preparation of Water-Soluble Soybean Polysaccharide (B)

(Example 2)

The water-soluble soybean polysaccharide (A) was dissolved in 0.5% saline, reprecipitated 3 times to an ethanol concentration of 50%, and desalted using an ion-exchange resin ("Amberlite IR-120B", product of Organo Co.) to obtain a water-soluble soybean polysaccharide (B).

Preparation of Water-Soluble Soybean Polysaccharide (C)

(Example 3)

After extraction of water-soluble soybean polysaccharide in the same process used for preparation of the water-soluble soybean polysaccharide (A), a water-soluble hemicellulose (C) was obtained without the purification treatment with an active carbon column.

The results of analysis of the water-soluble soybean polysaccharides obtained above were as follows.

| | Composition (%) | | |
|---|---|---|---|
| Component | Example 1 (A) | Example 2 (B) | Example 3 (C) |
| Water | 5.71 | 7.75 | 5.10 |
| Crude protein | 5.43 | 1.03 | 7.21 |
| Crude ash | 5.29 | 0.22 | 5.30 |
| Polysaccharides | 83.57 | 91.00 | 82.39 |
| Average molecular weight | 178000 | 207000 | 114000 |

The saccharide compositions of the water-soluble polysaccharides (A), (B) and (C) were then analyzed.
The results were as follows.

| | Saccharide composition (%) | | |
|---|---|---|---|
| Saccharide type | Example 1 (A) | Example 2 (B) | Example 3 (C) |
| Uronic acid | 20.4 | 16.9 | 19.4 |
| Rhamnose | 1.6 | 2.7 | 2.1 |
| Fucose | 2.7 | 5.2 | 3.9 |
| Arabinose | 19.9 | 20.1 | 23.1 |
| Xylose | 6.4 | 8.4 | 5.8 |
| Galactose | 47.3 | 45.8 | 43.4 |
| Glucose | 1.7 | 0.9 | 2.3 |

Animal Experiment

Four-week-old SD male rats, with 7 rats to a group, were raised for 3 weeks with free access to a diet consisting of AIN76 type purified feed which contained 5% water-soluble soybean polysaccharide or cellulose and 0.3% cholesterol oxide, and included 5% safflower oil. The composition of the cholesterol oxide blended with the feed was as follows.

| Cholesterol oxide mixture composition (%) | |
|---|---|
| 7α-hydroxycholesterol | 9.9 |
| cholesterol | 6.8 |
| 7β-hydroxycholesterol + 5β-epoxycholesterol | 13.3 |
| 5α-epoxycholesterol | 4.4 |
| cholestanetriol | 3.7 |
| 7-ketocholesterol | 10.2 |
| 25-hydroxycholesterol | 1.3 |
| unidentified oxidized steroids | 50.4 |

Upon completion of the 3 week raising period, blood was taken from the abdominal aorta, the rats were killed and their livers and blood were sampled. The lipid peroxide levels in the blood were measured by the TBA method, and then serum was prepared and the lipid parameters were measured with those of the liver. After TLC fractionation of the lipid classes of the serum and liver, the fatty acid composition was measured by GC. The cholesterol oxide levels in the liver and the neutral steroids in feces collected during the raising period (10th–11th day) were measured by GC-MS, and the activity of Δ6-desaturase, which is the liver linolic acid desaturation rate-determining enzyme, was measured by the tracer method.

As shown below, measurement of the weight of the rats upon completion of the raising period showed that all 3 groups which had been given the water-soluble soybean polysaccharide underwent a weight increase which was significantly higher than that of the control group, although there was no difference in the amount of food consumption.

This result demonstrated that the water-soluble soybean polysaccharide has a function of reducing growth inhibition caused by cholesterol oxide.

Weight increase and feed intake (mean ± standard deviation) (g)

|  | Initial weight | Final weight | Feed intake |
|---|---|---|---|
| Water-soluble soybean polysaccharide (A) (Example 1) | 110 ± 3 | 138 ± 2* | 15 ± 0 |
| Water-soluble soybean polysaccharide (B) (Example 2) | 110 ± 3 | 140 ± 3* | 15 ± 0 |
| Water-soluble soybean polysaccharide (C) (Example 3) | 110 ± 3 | 132 ± 2* | 15 ± 0 |
| Cellulose (control) | 110 ± 3 | 116 ± 5 | 15 ± 0 |

*Significant difference from cellulose group ($p < 0.05$)

As indicated below, the results of measurement of the lipid peroxide levels in the blood (TBARS) showed significantly lower values for all the groups given the water-soluble soybean polysaccharide compared to the control group given cellulose. This demonstrated that the water-soluble polysaccharide lowers blood lipid peroxides produced by cholesterol oxide.

TBARS value (nmol MDA/ml) (mean ± standard deviation)

| Water-soluble soybean polysaccharide (A) (Example 1) | 4.1 ± 0.1* |
|---|---|
| Water-soluble soybean polysaccharide (B) (Example 2) | 3.9 ± 0.3* |
| Water-soluble soybean polysaccharide (C) (Example 3) | 4.3 ± 0.1* |
| Cellulose (control) | 5.8 ± 0.2 |

*Significant difference from cellulose group ($p < 0.05$)

Also, as shown below for the serum lipid levels, the groups given the water-soluble soybean polysaccharide were found to have significantly higher levels of HDL-cholesterol, known as "good cholesterol". Consumption of cholesterol oxide has been reported to lower HDL-cholesterol levels, but this was mitigated by intake of the water-soluble soybean polysaccharide, demonstrating a normalizing effect on lipoprotein metabolism.

Serum lipid levels (mean ± standard deviation)

|  | HDL-cholesterol | Cholesterol |
|---|---|---|
| Water-soluble soybean polysaccharide (A) (Example 1) | 69.8 ± 5.7* | 74.6 ± 6.1 |
| Water-soluble soybean polysaccharide (B) (Example 2) | 68.5 ± 4.3* | 72.1 ± 5.2 |
| Water-soluble soybean polysaccharide (C) (Example 3) | 62.7 ± 1.3* | 69.8 ± 6.6 |
| Cellulose (control) | 40.3 ± 2.7 | 66.3 ± 5.5 |

*Significant difference from cellulose group ($p < 0.05$)

When the liver phospholipids and the serum cholesteryl ester fatty acid compositions were examined, the linolic acid desaturation index $[(18:3+20:3)/18:2]$ was found to be significantly lower compared to the control group, as shown below.

Linolic acid desaturation index (mean ± standard deviation)

$(18:3 + 20:3)/18:2$

| Liver phosphatidyl choline | |
|---|---|
| Water-soluble soybean polysaccharide (A) (Example 1) | 3.4 ± 0.1* |
| Water-soluble soybean polysaccharide (B) (Example 2) | 3.2 ± 0.2* |
| Water-soluble soybean polysaccharide (C) (Example 3) | 4.1 ± 0.5 |
| Cellulose (control) | 4.1 ± 0.4 |
| Liver phosphatidyl ethanolamine | |
| Water-soluble soybean polysaccharide (A) (Example 1) | 10.8 ± 0.3* |
| Water-soluble soybean polysaccharide (B) (Example 2) | 10.7 ± 0.2* |
| Water-soluble soybean polysaccharide (C) (Example 3) | 11.8 ± 0.5 |
| Cellulose (control) | 13.0 ± 0.6 |
| Serum cholesteryl esters | |
| Water-soluble soybean polysaccharide (A) (Example 1) | 5.0 ± 0.1* |
| Water-soluble soybean polysaccharide (B) (Example 2) | 5.1 ± 0.3* |
| Water-soluble soybean polysaccharide (C) (Example 3) | 6.2 ± 0.4* |
| Cellulose (control) | 7.6 ± 0.2 |

*Significant difference from cellulose group ($p < 0.05$)

Also, when the liver microsome Δ6-desaturase activity was measured, significantly lower activity was found compared to the control group, as shown below. Thus, it was demonstrated that the liver microsome desaturase activity reflects the liver phospholipids and the linolic acid desaturation index of serum cholesteryl esters.

Δ6-desaturase activity (pmol/min/mg protein) (mean ± standard deviation)

| Water-soluble soybean polysaccharide (A) (Example 1) | 365 ± 20* |
|---|---|
| Water-soluble soybean polysaccharide (B) (Example 2) | 351 ± 18* |
| Water-soluble soybean polysaccharide (C) (Example 3) | 395 ± 52 |
| Cellulose (control) | 510 ± 80 |

*Significant difference from cellulose group ($p < 0.05$)

These results show that the eicosanoid production induced by accelerated linolic acid desaturation accompanying cholesterol oxide intake can be suppressed by consumption of water-soluble soybean polysaccharides, and that the water-soluble soybean polysaccharides have an effect of preventing allergy and inflammation.

In addition, when the liver and fecal cholesterol oxide levels were measured, the major cholesterol oxide levels in the liver were found to be significantly lower with intake of the water-soluble soybean polysaccharides compared to the control group, as shown below. On the other hand, the cholesterol oxide levels excreted in the feces with intake of the water-soluble soybean polysaccharides showed a significant increase or tendency to increase compared to the control group. These results show that the water-soluble soybean polysaccharides inhibit absorption of cholesterol oxide in food leading to its excretion in the feces, suggesting that the physiological action of cholesterol oxide is also controlled.

Liver and fecal cholesterol oxide contents
(mean ± standard deviation)

| | Liver ($\mu$g/g) | Fecal (mg/g) |
|---|---|---|
| 7α-hydroxycholesterol | | |
| Water-soluble soybean polysaccharide (A) (Example 1) | 28 ± 15* | 0.34 ± 0.05* |
| Water-soluble soybean polysaccharide (B) (Example 2) | 25 ± 10* | 0.32 ± 0.02* |
| Water-soluble soybean polysaccharide (C) (Example 3) | 48 ± 12* | 0.29 ± 0.06* |
| Cellulose (control) | 110 ± 20* | 0.20 ± 0.01* |
| 7β-hydroxycholesterol + 5β-epoxycholesterol | | |
| Water-soluble soybean polysaccharide (A) (Example 1) | 60 ± 40* | 3.50 ± 0.55* |
| Water-soluble soybean polysaccharide (B) (Example 2) | 62 ± 32* | 3.21 ± 0.20* |
| Water-soluble soybean polysaccharide (C) (Example 3) | 150 ± 15* | 2.17 ± 0.43 |
| Cellulose (control) | 355 ± 43 | 1.30 ± 0.60 |
| 5α-epoxycholesterol | | |
| Water-soluble soybean polysaccharide (A) (Example 1) | 20 ± 8* | 1.30 ± 0.46 |
| Water-soluble soybean polysaccharide (B) (Example 2) | 12 ± 10* | 1.40 ± 0.68 |
| Water-soluble soybean polysaccharide (C) (Example 3) | 43 ± 28* | 0.70 ± 0.32 |
| Cellulose (control) | 148 ± 15 | 0.60 ± 0.22 |
| Cholestanetriol | | |
| Water-soluble soybean polysaccharide (A) (Example 1) | 17 ± 4* | 0.09 ± 0.02* |
| Water-soluble soybean polysaccharide (B) (Example 2) | 18 ± 3* | 0.08 ± 0.02* |
| Water-soluble soybean polysaccharide (C) (Example 3) | 23 ± 8 | 0.07 ± 0.01* |
| Cellulose (control) | 32 ± 8 | 0.04 ± 0.00 |
| 7-ketocholesterol | | |
| Water-soluble soybean polysaccharide (A) (Example 1) | 32 ± 5* | 0.54 ± 0.12* |
| Water-soluble soybean polysaccharide (B) (Example 2) | 22 ± 1* | 0.68 ± 0.15* |
| Water-soluble soybean polysaccharide (C) (Example 3) | 68 ± 8* | 0.51 ± 0.13 |
| Cellulose (control) | 366 ± 43 | 0.33 ± 0.08 |
| 25-hydroxycholesterol | | |
| Water-soluble soybean polysaccharide (A) (Example 1) | 13 ± 4* | 0.39 ± 0.05* |
| Water-soluble soybean polysaccharide (B) (Example 2) | 8 ± 4* | 0.41 ± 0.06* |
| Water-soluble soybean polysaccharide (C) (Example 3) | 25 ± 5* | 0.28 ± 0.04* |
| Cellulose (control) | 38 ± 6 | 0.19 ± 0.07 |

*Significant difference from cellulose group ($p < 0.05$)

Confirmation of Cholesterol Oxide Absorption Effect in Vitro

Figure 2:
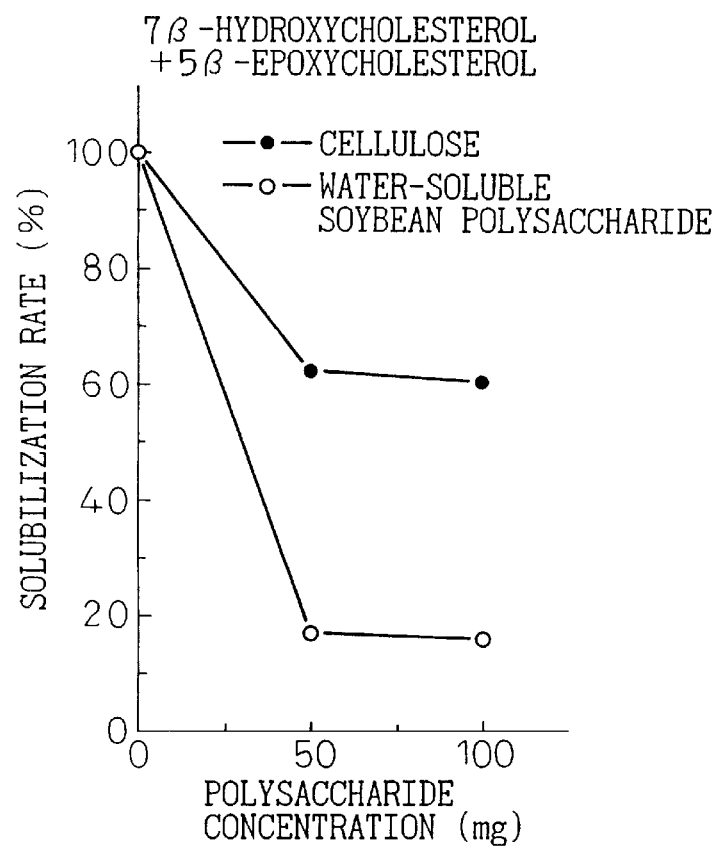
FIG. 2 is a graph showing the micelle solubilization rate for 7β-hydroxycholesterol+5β-epoxycholesterol.
Figure 3:
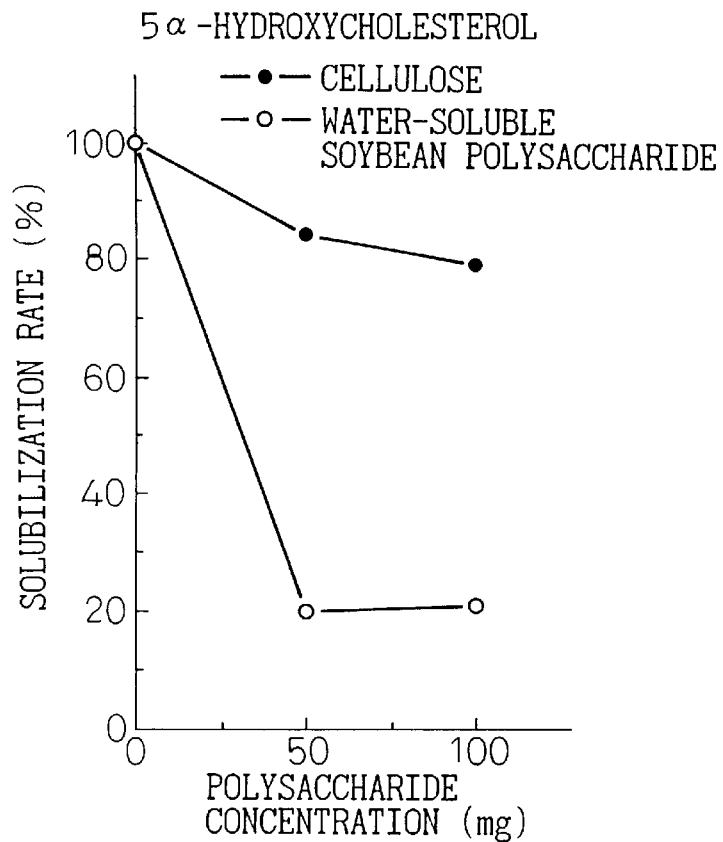
FIG. 3 is a graph showing the micelle solubilization rate for 5α-epoxycholesterol.
Figure 4:
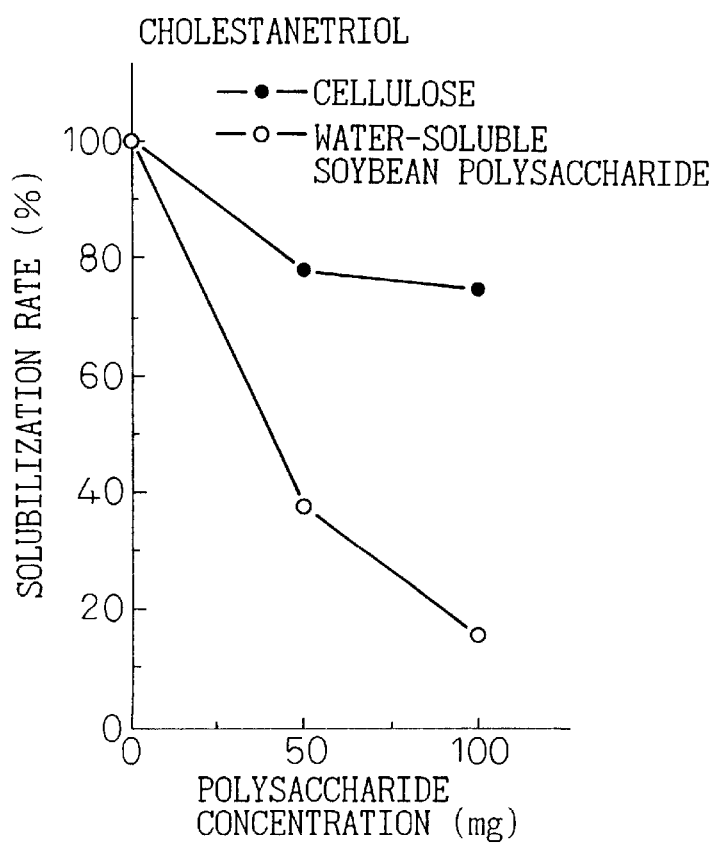
FIG. 4 is a graph showing the micelle solubilization rate for cholestanetriol.
Figure 5:
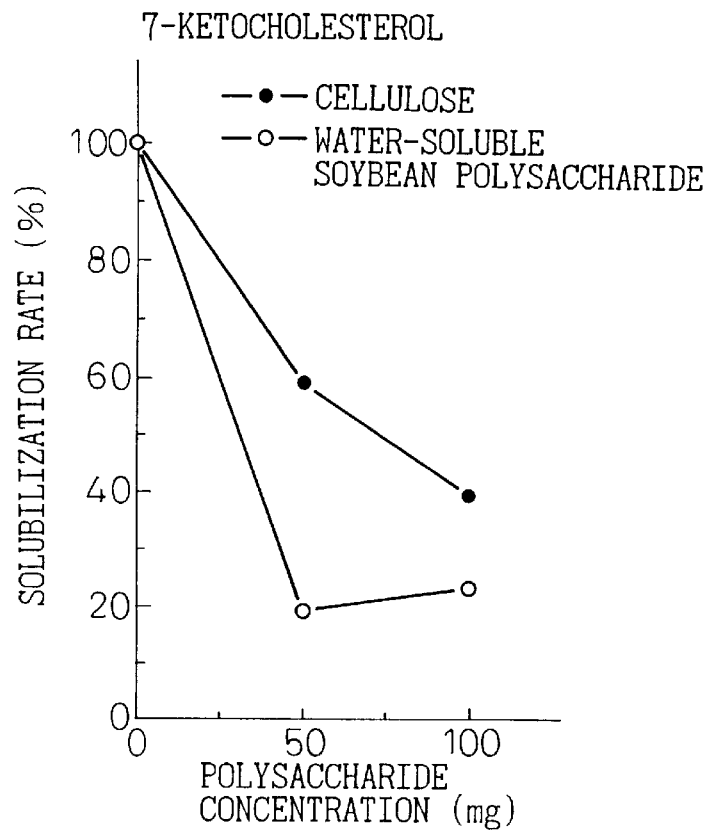
FIG. 5 is a graph showing the micelle solubilization rate for 7-ketocholesterol.
Figure 6:
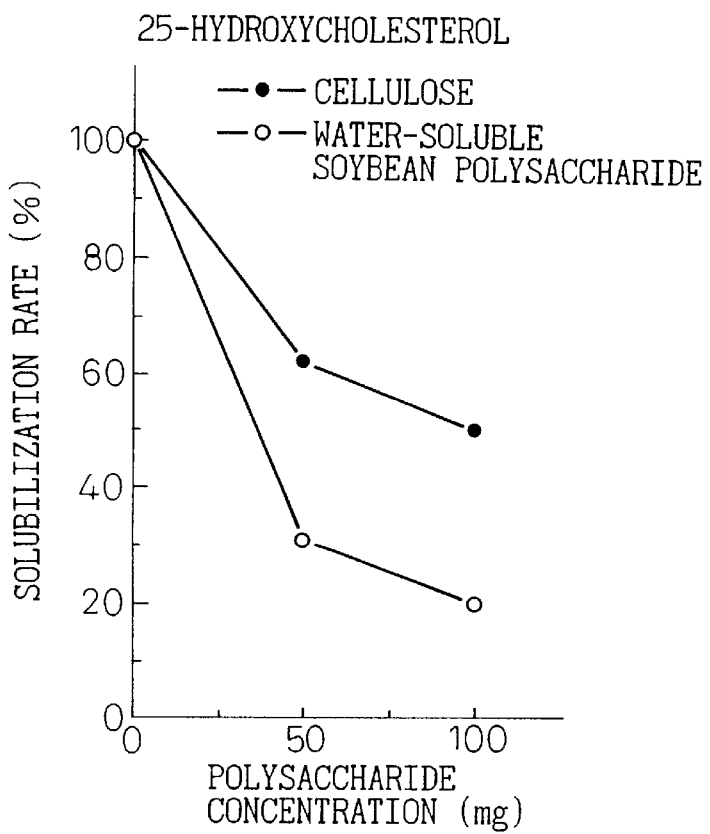
FIG. 6 is a graph showing the micelle solubilization rate for 25-hydroxycholesterol.

The water-soluble soybean polysaccharide (A) or cellulose was added to micelles containing cholesterol oxide, and the added polysaccharide concentration and the amount of cholesterol oxide solubilized in the micelles were measured. The results in FIG. 1 to FIG. 6 show that addition of the water-soluble soybean polysaccharide (A) inhibits the major micelle solubilization of cholesterol oxide in a concentration-dependent manner.

Water-soluble soybean polysaccharides adsorb physically harmful cholesterol oxide or adsorb bile acids, thus inhibiting micelle solubilization of cholesterol oxide to reduce its absorption in the small intestine; they can therefore serve as food components which act against lower body homeostasis induced by ingested lipid peroxides.

We claim:

1. A method of adsorbing cholesterol oxide comprising the step of adding a plant-derived water-soluble polysaccharide to foods containing cholesterol oxide, wherein the water-soluble polysaccharide is obtained by extracting soybean seeds with water under acidic conditions, at a pH near the isoelectric point of protein in the soybean seeds and at a temperature within the range of from 80° C. to 130° C.

2. A process for producing foods free of cholesterol oxide comprising the step of adding a plant-derived water-soluble polysaccharide to foods containing cholesterol oxide, wherein the water-soluble polysaccharide is obtained by extracting soybean seeds with water under acidic conditions, at a pH near the isoelectric point of protein in the soybean seeds and at a temperature within the range of from 80° C. to 130° C.

3. The process of claim 2 wherein the food is an animal oil, a livestock or marine product, or butter, margarine, shortening, cream, mayonnaise or a sauce.

* * * * *